United States Patent [19]

Williams, III

[11] Patent Number: 5,704,350

[45] Date of Patent: Jan. 6, 1998

[54] NUTRITIONAL MICROCOMPUTER AND METHOD

[75] Inventor: William B. Williams, III, Albemarle, N.C.

[73] Assignee: Nutritec Corporation, Albemarle, N.C.

[21] Appl. No.: 217,685

[22] Filed: Mar. 25, 1994

[51] Int. Cl.[6] .................................................. G06F 15/40
[52] U.S. Cl. ..................... 128/630; 128/921; 364/709.02
[58] Field of Search ........................ 364/413.29, 709.03, 364/410, 709.12, 401; 434/127

[56] References Cited

U.S. PATENT DOCUMENTS

| | | |
|---|---|---|
| 3,626,377 | 12/1971 | Markley . |
| 4,095,274 | 6/1978 | Gordon . |
| 4,101,071 | 7/1978 | Brejnik et al. . |
| 4,159,416 | 6/1979 | Brejnik et al. . |
| 4,192,000 | 3/1980 | Lipsey . |
| 4,244,020 | 1/1981 | Ratcliff .............................. 364/413.29 |
| 4,321,674 | 3/1982 | Krames et al. .................... 364/413.29 |
| 4,380,802 | 4/1983 | Segar et al. ....................... 364/413.29 |
| 4,575,804 | 3/1986 | Ratcliff .............................. 364/413.29 |
| 4,686,624 | 8/1987 | Blum et al. . |
| 4,796,182 | 1/1989 | Duboff ............................... 364/413.19 |
| 4,855,945 | 8/1989 | Sakai ................................. 364/413.29 |
| 4,891,756 | 1/1990 | Williams, III ..................... 364/413.29 |
| 4,894,793 | 1/1990 | Ikemoto et al. ................... 364/413.29 |
| 4,954,954 | 9/1990 | Madsen et al. .................... 364/413.29 |
| 5,033,561 | 7/1991 | Hettinger .......................... 364/413.29 |
| 5,233,520 | 8/1993 | Kretsch et al. .................... 364/413.29 |
| 5,387,164 | 2/1995 | Brown, Jr. ................................. 482/9 |

FOREIGN PATENT DOCUMENTS 60-146356  8/1985  Japan .

OTHER PUBLICATIONS

Sally Squires, "Improving Diet, Byte by Byte", *Washington Post Health*, Jan. 30, 1985, one page.
"DietCoach", one page.

*Primary Examiner*—Gail O. Hayes
*Assistant Examiner*—Krishna Kalidindi
*Attorney, Agent, or Firm*—Shefte, Pinckney & Sawyer

[57] ABSTRACT

This invention relates to a microcomputer and method for selecting foodstuffs from a foodstuff database, nutrients from a nutrient database, minerals from a mineral database, vitamins from a vitamin database and physical activities from a physical activity database, maintaining a record of the foodstuffs, nutrients, minerals and vitamins eaten and the physical activities exercised, and by computational means to analyze the selected and recorded foodstuff, nutrient, mineral and vitamin nutritional data along with the selected and recorded physical activities exercised to compare the user's daily dietary and physical activities to the user's RDA (recommended dietary allowance).

42 Claims, 10 Drawing Sheets

Fig. 2

```
           USER LIST
        Select or Add a Name
        1. JANICE
        2. BAXTER
        3. LEE-ANNE
        4. NOT USED
        5. NOT USED
        COMMAND & SELECTION LINE
```

Fig. 3

```
        PHYSICAL INFORMATION
        NAME     [      ]
        AGE      [   ]  SEX [ ]
        HEIGHT   [   ] FT [ ] IN
        WEIGHT   [   ] LBS
        ACTIVITY [      ]
        COMMAND & SELECTION LINE
```

Fig. 4

```
        PHYSICAL INFORMATION
        NAME     [BILL]
        AGE      [51]  SEX [M]
        HEIGHT   [6]   [0]
        WEIGHT   [310]
        ACTIVITY [LIGHT]
        COMMAND & SELECTION LINE
```

Fig. 5

| PERSONAL RDA FOR - BILL | |
|---|---|
| % OF CALORIES | DAILY NET |
| KCAL  100  kc | 3520 kc |
| FAT   29% | 39.1 gm |
| CARB  53% kc | 468.1 gm |
| PROT  16% kc | 148.0 gm |
| CHOL | 300 gm |
| COMMAND & SELECTION LINE | |

| FISH / SHELLFISH |
|---|
| SELECT FOOD ITEM |
| 1. ABALONE - FRIED |
| 2. ABALONE - RAW |
| 3. BASS, FRESHWATER - RAW |
| 4. BASS, STRIPED - RAW |
| 5. BLUEFISH - RAW |
| COMMAND & SELECTION LINE |

Fig. 10

| SWAP |
|---|
| BASS, STRIPED - RAW |
| 1. CRAB, BLUE - BLD/STM |
| 2. GROUPER - RAW |
| 3. LOBSTER, NRTH-BLD/STM |
| 4. OCEAN PERCH, ALT - RAW |
| 5. PIKE, WALLEYE - RAW |
| COMMAND & SELECTION LINE |

Fig. 11

| BASS, STRIPED - RAW | |
|---|---|
| MODIFY PORTION | |
| USA | 1 oz |
| SERVING | oz |
| COMMAND & SELECTION LINE | |

Fig. 12

| BASS, STRIPED - RAW | | |
|---|---|---|
| USDA | | 4 oz |
| KCAL | 100 kc | 100 kc |
| FAT | 22% kc | 2.6 gm |
| CARB | 0% kc | 0 gm |
| PROT | 73% kc | 20.1 gm |
| CHOL | | 35.0 mg |
| COMMAND & SELECTION LINE | | |

Fig. 13

| MINERAL SELECTION | | |
|---|---|---|
| 1. SODIUM | | mg |
| 2. POTASSIUM | | mg |
| 3. MAGNESIUM | | mg |
| 4. IRON | | mg |
| 5. ZINC | | mg |
| 6. CALCIUM | | mg |
| COMMAND & SELECTION LINE | | |

Fig. 18

| VITAMIN SELECTION | | |
|---|---|---|
| 1. VIT A | | IU |
| 2. VIT B | | IU |
| 3. VIT B6 | | IU |
| 4. VIT B12 | | IU |
| 5. VIT C | | IU |
| 6. VIT K | | IU |
| COMMAND & SELECTION LINE | | |

Fig. 19

| FOOD INQUIRY ONLY |
|---|
| SELECT FOOD GROUP |
| 1. MEATS |
| 2. VEGETABLES |
| 3. DAIRY & EGGS |
| 4. CEREALS |
| 5. FRUIT-BERRY-JUICE |
| COMMAND & SELECTION LINE |

Fig. 20

| NUTRIENT HISTORY |
|---|
| 1. NUTRITION PERCENTAGES |
| 2. RDA COMPARISONS |
| |
| COMMAND & SELECTION LINE |

Fig. 21

|  AVERAGE CONSUMPTION  |||
|---|---|---|
| TODAY | LAST | DAYS |
| NET CALORIES | | 1958 kc |
| % OF CALORIES | | TOTALS |
| KCAL 100 kc | | 2425 kc |
| FAT 29% gm | | 25.1 gm |
| CARB 53% gm | | 324.1 gm |
| COMMAND & SELECTION LINE |||

Fig. 22

|  RDA COMPARISON  |||
|---|---|---|
| TODAY | LAST | DAYS |
| NET CALORIES | | 1958 kc |
| RDA | | AVG TOT |
| KCAL 3520 kc | | 2425 kc |
| FAT 39. gm | | 25.1 gm |
| CARB 468. gm | | 324.1 gm |
| COMMAND & SELECTION LINE |||

Fig. 23

| DIET GOAL & ACTIVITIES |
|---|
| 1. DIET GOAL |
| 2. ACTIVITIES LIST |
| |
| COMMAND & SELECTION LINE |

Fig. 24

| DIET GOAL FOR BILL |
|---|
| 5 LBS IN 20 DAYS |
| CURRENT WEIGHT 334 LBS |
| CURRENT RDA 3520 KC |
| GOAL DIFFERENCE PER DAY |
| 875 KC |
| COMMAND & SELECTION LINE |

Fig. 25

```
        REPORT FOR BILL

TO LOSE 5 LBS IN 20 DAYS:
      DECREASE DAILY CALORIC
      INTAKE AND/OR INCREASE
        PHYSICAL ACTIVITY BY
               875 KC

COMMAND & SELECTION LINE
```

Fig. 26

```
        ACTIVITIES LIST
KCAL BURN FOR    30       MIN
AEROBICS-HEAVY           606
AEROBICS-LIGHT           227
ARCHERY                  266
BACK-PACKING             681
BADMINTON-DOUBLE         698
    COMMAND & SELECTION LINE
```

Fig. 27

```
    TODAYS CALORIC NET TOTAL

CALORIC INTAKE        [    ]
CALORIC BURN-OFF      [    ]

NET CALORIC TOTAL     [    ]

COMMAND & SELECTION LINE
```

Fig. 28

```
        PHYSICAL ACTIVITY

1. ADD TO TODAY'S TOTAL
    2. SUBTRACT FROM TOTAL
    3. SELECT ANOTHER
    4. PRIMARY MENU

COMMAND & SELECTION LINE
```

Fig. 29

```
        CUSTOM FOOD DESIGN

ADD FOOD
           ADD MEAL
           ADD RECIPE

COMMAND & SELECTION LINE
```

Fig. 30

```
              ADD FOOD
           ENTER FOOD DATA
   FOOD NAME
   FOOD UNITS
   KCAL                    0    kc
   FAT                   0.0    gm
   CARB                  0.0    gm
        COMMAND & SELECTION LINE
```

Fig. 31

```
              ADD MEAL
   FOOD NAME
         SELECT FOOD ITEMS
   NOT USED
   NOT USED
   NOT USED
   NOT USED
        COMMAND & SELECTION LINE
```

Fig. 32

```
             ADD RECIPE
   RECIPE NAME
         SELECT FOOD ITEMS
   NOT USED
   NOT USED
   NOT USED
   NOT USED
        COMMAND & SELECTION LINE
```

Fig. 33

PERSONAL DATA

1. PHYSICAL INFORMATION
2. PERSONAL RDA
3. WEIGHT RECORD

COMMAND & SELECTION LINE

Fig. 34

WEIGHT RECORD

ENTER TODAY'S WEIGHT

AVERAGE WEIGHT FOR LAST [ ] DAYS

COMMAND & SELECTION LINE

Fig. 35

COMPUTER CONTROLS

1. TIME
2. DATE
3. CONTRAST
4. AUTO OFF

COMMAND & SELECTION LINE

Fig. 36

NUTRITIONAL MICROCOMPUTER AND METHOD

BACKGROUND OF THE INVENTION

This invention relates to a microcomputer and method for selecting foodstuffs, individual nutrients, minerals, and vitamins eaten and a method for selecting physical activities and maintaining a record of caloric expenditure of the physical activity exercised over a period of time by a specific user.

Many persons must select foods to eat based upon dietary restrictions imposed by desired weight control or by physician's prescriptions for maintaining health. It is now regarded by the medical profession that the best way to lose weight and to keep it off is by a daily lifestyle change using a sensible combination of diet and exercise. Many aids have been proposed by persons engaged in such selection and recording of foodstuffs eaten, including at least some computerized record keeping schemes as shown, for example, in Radcliff U.S. Pat. No. 4,244,020; Krames U.S. Pat. No. 4,321,674; Segar U.S. Pat. No. 4,380,802; Ratcliff U.S. Pat. No. 4,575,804; Blum U.S. Pat. No. 4,686,624; and Williams U.S. Pat. No. 4,891,756.

Such devices and methods known prior to the present invention suffer from a number of difficulties and deficiencies. Most notable is the limitation on the usage of the nutritional values of specific foodstuffs, the usage of the values of individual nutrients, minerals and vitamins and the usage of physical activities, in constructing a sensible diet and health regimentation best suited to the user's benefit: more specifically is the limitation on the ability to establish the RDA (recommended dietary allowance) of an individual user from a plurality of users; the limitation of comparing the consumption of foodstuffs, nutrients, minerals and vitamins over periods of time to that individual's RDA; and the limitation of achieving a daily net caloric total, as calculated by subtracting the daily caloric expenditure of selected physical activities from the daily consumption of selected foodstuffs. RDA is accepted by the nutritional industry as the established dietary requirement of an individual. In Williams U.S. Pat. No. 4,891,756, nutritional value information of a large quantity of foodstuffs was easily accessed, displayed, selected and registered over a selected period of time, but was deficient in comparison of that selected foodstuff nutritional value information to the user's RDA and to the correlation of the caloric expenditure of selected physical activities.

This invention will afford the user the ability to make competent and rational dietary and exercise decisions by timely comparisons of dietary and exercise activities to his or her RDA.

SUMMARY OF THE INVENTION

With the foregoing in mind, it is an object of this invention to provide an apparatus and method enabling a person who chooses to exercise care in selecting a diet to be well advised regarding the nutritional values of foodstuffs, nutrients, minerals, and vitamins available for consumption and regarding the caloric expenditure of selected physical activities.

In realizing this object of the present invention, in one embodiment, a hand held microcomputer is contemplated in which databases of information regarding a large number of possible foodstuffs, nutrients, minerals, vitamins and physical activities are registered and maintained in a form organized to permit ease of access to the information. More particularly, the nutritional information is organized within the database by groupings of foodstuffs by type and, in some regards, by source. The individual nutrients, minerals, vitamins, and physical activities are organized in separate databases of their own.

Yet a further object of this invention is to enable a user of the apparatus contemplated by this invention to select and view information regarding a number of foodstuffs by progression through groupings displayed and organized to permit access first to a plurality of types of foods, then to a plurality of foods within a common group, and then to detailed nutritional information about a specific selected food. In realizing this object of the present invention, data regarding a number of foods may be entered into and maintained in a database having a particular hierarchic structure.

Yet a further object of this invention is to enable a user of the apparatus contemplated by this invention to select and view information regarding a number of nutrients, minerals, vitamins and physical activities. In realizing this object of the present invention, separate databases of large numbers of nutrients, minerals, vitamins and physical activities may be registered and maintained in a form organized to permit ease of access to the information.

Yet a further object of this invention is to permit a user of the apparatus contemplated by this invention to accumulate a record over time of the nutritional values of the foodstuffs, nutrients, minerals, and vitamins ingested and of the physical activities selected. In realizing this object of the present invention, provision may be made for registering the information related to a specific selected foodstuff, nutrient, mineral, vitamin or physical activity and accumulating over an interval of time the information relating to the foodstuffs, nutrients, mineral, vitamins and physical activities selected over that interval.

Yet a further object of this invention is to permit a user of the apparatus contemplated by this invention to establish and record the user's personal RDA of the nutritional values of nutrients, minerals and vitamins using the Harris-Benedict formula entering the user's personal and physical characteristics regarding name, age, sex, weight, height, and activity level. In realizing this object of the present invention, provision is made for viewing, correcting and registering the user's RDA information.

Yet a further object of this invention is to permit a user of the apparatus contemplated by this invention to view and register the user's distinctive rate of caloric expenditure regarding each physical activity in the physical activity database. In realizing this object of the present invention, data regarding a number of physical activities may be entered into and maintained in a database where the pre-established hourly rate of caloric expenditure of each physical activity is factored by the weight of the user.

Yet a further object of this invention is to permit a user of the apparatus contemplated by this invention to view and compare the nutritional gram weight unit value and/or international unit value information of the user's RDA to the user's daily accumulated or anticipated accumulation of nutritional gram weight unit value and/or international unit value information regarding selection or anticipated selection of foodstuffs, nutrients, minerals and vitamins, over a period of time, allowing the user to make value judgments regarding the selection or anticipated selection of foodstuffs, nutrients, minerals and vitamins. In realizing this object of the present invention, provision may be made for selecting and viewing the registered nutritional gram weight unit value information and/or international unit value information regarding selection or anticipated selection of foodstuffs, nutrients, minerals and vitamins, over a period of time.

Yet a further object of this invention is to permit a user of the apparatus contemplated by this invention to view and compare the user's RDA percentages of caloric unit value information regarding the nutritional elements of fat, carbohydrate and protein, to the user's percentages of daily accumulated or anticipated accumulation of caloric value information in the selection or anticipated selection of foodstuffs and nutrients regarding the nutritional elements of fat, carbohydrate and protein, over a period of time, allowing the user to make value judgments regarding the selection or anticipated selection of foodstuffs and nutrients. In realizing this object of the present invention, provision may be made for selecting and viewing the user's registered RDA percentage of caloric unit value information regarding the nutritional elements of fat, carbohydrate and protein and the user's registered daily accumulated or anticipated accumulation of percentages of caloric value information in the selection or anticipated selection of foodstuffs and nutrients regarding the nutritional elements of fat, carbohydrate and protein, over a period of time.

Yet a further object of this invention is to permit a user of the apparatus contemplated by this invention to view the user's accumulated daily averages, over a selected period of time, of the daily accumulation of nutritional unit values of gram weight and/or international unit information regarding the selection of foodstuffs, nutrients, minerals and vitamins, and the daily averages, over the same selected period of time, of other daily accumulated caloric expenditure of selected physical activities. In realizing this object of the present invention, provision may be made for selecting and viewing the daily averaged accumulation of registered daily nutritional data information and daily physical activity expenditure data information regarding the selection of foodstuffs, nutrients, minerals, vitamins and physical activities.

Yet a further object of this invention is to permit a user of the apparatus contemplated by this invention to view the user's accumulated daily averages, over a selected period of time, of the daily accumulation of the percentages of caloric unit value information in the selection of foodstuffs and nutrients regarding the nutritional elements of fat, carbohydrate and protein, and the daily averages, over the same period of time, of the daily accumulated caloric expenditure of elected physical activities. In realizing this object of the present invention, provision may be made for selecting and viewing the daily average percentage accumulation of registered daily nutritional data information and daily physical activity caloric expenditure data information regarding the selection of foodstuffs, nutrients, minerals, vitamins and physical activities.

Yet a further object of this invention is to permit a user of the apparatus contemplated by this invention to initiate a diet plan whereby the user could estimate the necessary daily reduction of caloric value information regarding the ingestion of selected foodstuffs and nutrients, to lose a predetermined number of pounds of body weight over a predetermined interval of time; or estimate the necessary daily expenditure of caloric value information regarding the selection of physical activities, to lose a predetermined number of pounds of body weight over a predetermined interval of time, or a combination of daily reduction of caloric value information regarding the ingestion of selected foodstuffs and nutrients, and daily expenditure of caloric value information regarding the selection of physical activities, to lose a predetermined number of pounds of body weight over a predetermined interval of time. In realizing this object of the present invention, provision may be made for registering the daily caloric value expenditure necessary to reduce one pound of body weight factored by the predetermined number of pounds of body weight the user desires to lose divided by the user's predetermined interval of time in days, displaying related conclusive information.

Yet a further object of this invention is to permit a user of the apparatus contemplated by this invention to display and register the daily accumulated net caloric value information in comparison to the user's RDA regarding total daily caloric value information. In realizing this object of the present invention, provision may be made to access the registered daily accumulated caloric value information regarding selected foodstuffs and nutrients, access and subtract the registered daily accumulated caloric value expenditure information regarding selected physical activities from the registered daily accumulated caloric value information regarding selected foodstuffs and nutrients, displaying and registering the daily accumulated net caloric value information.

Yet a further object of this invention is to permit a user of the apparatus contemplated by this invention to select and view information regarding a number of nutrients, minerals, and vitamins to permit accumulation of the value information regarding selected nutrients, minerals and vitamins to the accumulated nutritional value information of foodstuffs previously or subsequently selected. In realizing this object of the present invention, data regarding a number of nutrients may be entered into and organized in a form to permit ease of access, data regarding a number of minerals is entered into and organized in a form to permit ease of access, and data regarding a number of vitamins is entered into and organized in a form to permit ease of access.

Yet a further object of this invention is to permit a user of the apparatus contemplated by this invention to exchange or swap a displayed foodstuff for another foodstuff within the same food group using the gram weight value information of fat and the total caloric value information of the selected and displayed foodstuff as criteria. In realizing this object of the present invention, the foodstuff database may be entered into and the foodstuff meeting the required criteria may be selected and displayed.

Yet a further object of this invention is to permit a user of the apparatus contemplated by this invention to append to the foodstuff database a foodstuff that is not included in the foodstuff database along with its corresponding nutritional value information. In realizing this object of the present invention, a display may be exhibited permitting manual entry of the foodstuff name, serving size, and nutritional value information.

Yet a further object of this invention is to permit a user of the apparatus contemplated by this invention to append a meal as if it were a singular foodstuff composed of several foodstuffs and corresponding nutritional value information, registered in a meal foodstuff database in a form organized to permit ease of access to the information. In realizing this object of the present invention, a display may be exhibited permitting manual entry of the meal identifying name and selected foodstuffs from the foodstuff database.

Yet a further object of this invention is to permit a user of the apparatus contemplated by this invention to append a recipe as if it were a singular foodstuff composed of several foodstuffs and corresponding nutritional value information, registered in a recipe foodstuff database in a form organized to permit ease of access to the information. In realizing this object of the present invention, a display may be exhibited permitting manual entry of the recipe identifying name and selected foodstuffs from the foodstuff database.

Yet a further object of this invention is to permit a user of the apparatus contemplated by this invention to view the user's monthly averaged body weight and updated RDA corrected by the last weight registered. In realizing this object of the present invention, a display may be exhibited permitting manual entry of body weight at the user's discretion, time of entry is recorded and sequential entries of body weight replaces that portion of the user's RDA.

Yet a further object of this invention is to permit a user of the apparatus contemplated by this invention to register information simultaneously. In realizing this object of the present invention, a display may be exhibited permitting manual entry of the user's name whose identity at initialization of the computer will allow continuous revision of registered information regarding entries and selections by the identified user.

These and other objects of the present invention are accomplished with nutritional microcomputer apparatus is disclosed which comprises a memory device for receiving and retaining databases of information regarding foodstuffs, nutrients, minerals, vitamins and physical activities; an accessing device for accessing from the memory device foodstuff identifying information regarding a selected group of foodstuffs from among those in the database, nutrient identifying information regarding a selected nutrient from among those in the database, mineral identifying information regarding a selected mineral from among those in the database, vitamin identifying information regarding a selected vitamin from among those in the database and physical activity identifying information regarding a selected physical activity from among those in the database; a display device for displaying a plurality of lines of information for a corresponding plurality of foodstuffs, nutrients, minerals, vitamins and physical activities accessed from the memory device by the accessing device; a selection device for selecting from the display of a plurality of lines of information that foodstuff identifying and nutritional value information and which relates at least one of: a specific nutrient to nutrient identifying and nutrient value information, a specific mineral to mineral identifying and mineral value information, a specific vitamin to vitamin identifying and vitamin value information and a specific physical activity to physical activity identifying and physical activity value information; and a register device for registering the information selected from the display regarding a specific foodstuff and at least one of nutrient, mineral, vitamin and physical activity and for accumulating over an interval of time the information regarding additional selected foodstuffs and at least one nutrients, minerals, vitamins and physical activities.

The memory device may retain information regarding the caloric content of foodstuffs. The memory device may retain information regarding the protein content of foodstuffs. The memory device may retain information regarding the carbohydrate content of foodstuffs. The memory device may retain information regarding the fat content of foodstuffs.

The memory device may retain information regarding the sodium content of foodstuffs. The memory device may retain information regarding the cholesterol content of foodstuffs. The memory device may retain information regarding the fiber content of foodstuffs. The memory device may retain information regarding at least one mineral contained in the foodstuffs. The memory device may retain information regarding at least one vitamin contained in the foodstuffs. The memory device may retain information regarding the brand names of specific foodstuff products.

The memory device may retain information regarding the serving size of foodstuffs, nutrients, vitamins and minerals. The accessing device may select, on repeated actuation, from among the information retained in the memory device those elements of information which relate to a series of selected groups of related foodstuffs, each group being displayed as actuation of the accessing device is repeated.

The display device may display a predetermined number of lines of information each having a predetermined number of characters and the accessing device may cause the display of at least one of: foodstuff identifying information absent nutritional value information, nutrient identifying information absent nutritional value information, mineral identifying information absent nutritional value information, vitamin identifying information absent nutritional value information, and physical activity identifying information absent caloric value information.

The selection device may cause the display of at least one of: foodstuff identifying and nutritional value information for a single selected foodstuff, nutrient identifying and nutritional value information for a single selected nutrient, mineral identifying and nutritional value information for a single selected mineral, vitamin identifying and nutritional value information for a single selected vitamin, and physical activity identifying and caloric value information for a single selected physical activity.

The register device may accumulate totals of nutritional and/or caloric values for at least one of: selected foodstuffs, nutrients, minerals, vitamins and physical activities over at least one of: daily intervals and an accumulation of daily intervals.

A nutritional microcomputer apparatus comprising a memory device for receiving and retaining a database of foodstuff identifying and nutritional value information regarding a plurality of classes of foodstuffs, the nutritional value information comprising information on content of calories, protein, carbohydrates, fat, sodium, cholesterol, fiber, at least one mineral and at least one vitamin, and for receiving and retaining a database of at least one of: nutrient identifying and nutritional value information regarding an individual nutrient, the nutritional value information comprising information on content of calories, protein, carbohydrates, fat, sodium, cholesterol, fiber, at least one mineral and at least one vitamin; a database of mineral identifying and nutritional value information regarding an individual mineral, the nutritional value information comprising information on unit content of the mineral; a database of vitamin identifying and nutritional value information regarding an individual vitamin, the nutritional value information comprising information on unit content of the mineral; and a database of physical activity identifying and caloric value information regarding an individual physical activity and the caloric value information comprising caloric expenditure excised by the physical activity is disclosed.

An accessing device is also included for accessing from the memory device foodstuff identifying information regarding one selected group of foodstuffs from among those in the database; and at least one of nutrient identifying information regarding one selected nutrient from among those in the database; mineral identifying information regarding one selected mineral from among those in the database; vitamin identifying information regarding one selected vitamin from among those in the database; and physical activity identifying information regarding one selected physical activity from among those in the database. A display device is included for displaying a plurality of lines of foodstuff identifying information, and at least one of: nutrient identifying information, mineral identifying information, vitamin identifying information and physical activity identifying information for a corresponding plurality of foodstuffs, nutrients, minerals, vitamins, and physical activities accessed from the memory by the accessing device.

A selection device is also employed for selecting from the display of a plurality of lines of information that foodstuff identifying and nutritional value information which relates to a specific foodstuff; and at least one of: that nutrient identifying and nutritional value information which relates to a specific nutrient; that mineral identifying and nutritional value information which relates to a specific mineral; that vitamin identifying and nutritional value information which relates to a specific vitamin; and that physical activity identifying and caloric value information which relates to a specific physical activity.

A register device registers the information selected from the display regarding a specific foodstuff, and at least one of: a specific nutrient, mineral, vitamin and physical activity and for accumulating over at least one of: a daily interval and an accumulation of daily intervals the information regarding the selected foodstuffs, nutrients, minerals, vitamins and physical activities.

A method of recording the nutritional values of foodstuffs, nutrients, minerals, and vitamins selected for consumption and the caloric expenditure of physical activities, is disclosed comprising the steps of entering into and retaining in a database memory information regarding nutritional values for a plurality of groups of foodstuff types each composing a number of individual foodstuffs and entering into and retaining in a database memory information regarding at least one of: nutritional values for a plurality of nutrients, nutritional values for a plurality of minerals, nutritional values for a plurality of vitamins, and caloric value expenditures for a plurality of physical activities; accessing from the database memory foodstuff identifying information regarding a selected group of foodstuffs from among those in the database, and accessing from the database memory at least one of: nutrient identifying information regarding a selected nutrient from among those in the database, mineral identifying information regarding a selected mineral from among those in the database, vitamin identifying information regarding a selected vitamin from among those in the database, and physical activity identifying information regarding a selected physical activity from among those in the database; displaying a plurality of lines of information for a corresponding plurality of foodstuffs, and at least one of the nutrients, minerals, vitamins and physical activities accessed from said database memory; selecting from the display of said plurality of lines of information; that foodstuff identifying and nutritional value information which relates to a specific foodstuff; and at least one of: that nutrient identifying and nutritional value information which relates to a specific nutrient; that mineral identifying and nutritional value information which relates to a specific mineral; that vitamin identifying and nutritional value information which relates to a specific vitamin; and that physical activity identifying and caloric value information which relates to a specific physical activity identifying and caloric value information which relates to a specific physical activity; and registering the information from the display regarding a specific foodstuff, and at least one of: a specific nutrient, mineral, vitamin and physical activity and accumulating over an interval of time the information regarding additional selected foodstuffs, and at least one of: additional selected nutrients, minerals, vitamins and physical activities.

Information may be entered regarding the caloric content of foodstuffs and nutrients.

Information may be entered regarding the protein content of foodstuffs. Information may be entered regarding the carbohydrate content of foodstuffs.

Information may be entered regarding the fat content of foodstuffs. Information may be entered regarding the sodium content of foodstuffs. Information may be entered regarding the cholesterol content of foodstuffs. Information may be entered regarding the fiber content of foodstuffs. Information may be entered regarding the mineral content of foodstuffs. Information may be entered regarding the vitamin content of foodstuffs. Information may be entered regarding the unit value content of minerals. Information may be entered regarding the unit value content of vitamins. Information may be entered regarding the caloric expenditure values excised from physical activities. Information may be entered regarding the brand names of specific foodstuff products. Information may be entered regarding the serving size of foodstuffs. The steps of accessing identifying information may select from among the information retained in the database memory those elements of information which relate to a selected group of related foodstuffs. The steps of accessing identifying information may comprise selecting, on repeated actuation, from among the information retained in the memory device those elements of information which relate to a series of selected groups of related foodstuffs, each group being displayed as actuation of an accessing key is repeated.

The steps of accessing information may cause the display of foodstuff identifying nutritional value information for a single selected foodstuff and at least one of: nutrient identifying and nutritional value information which relates to a specific nutrient; mineral identifying and nutritional value information which relates to a specific mineral; vitamin identifying and nutritional value information which relates to a specific vitamin; and physical activity identifying and caloric value information which relates to a specific physical activity.

The steps of registering may comprise accumulating totals of nutritional values for selected foodstuffs and at least one of: nutrients, minerals, vitamins and caloric value expenditures for selected physical activities over at least one of: daily intervals and an accumulation of daily intervals. The step of computing the user's RDA of nutritional identifying and value information regarding nutrients, minerals, vitamins and physical activities using the Harris-Benedict Equation, by entering the user's personal and physical characteristics regarding name, age, sex, weight, height and activity level, and is registered in a user identifying database from which it may be accessed and displayed may also be included.

The step of computing the user's accumulated caloric value information of the foodstuff and nutrient identifying elements of fat, carbohydrates and protein each as a percentage of total calories of the caloric sum of those identifying elements as well as gram weight value information, and registering and displaying as daily value information and/or averaged daily value information over an interval of time may also be included.

The steps of computing the user's caloric expenditure value, regarding a selected physical activity from among those in the physical activity database, by factoring the weight of the user, the number of minutes exercised and the pre-established hourly rate of caloric expenditure for each physical activity, and registering said caloric expenditure in a user identifying database from which it may be accessed and displayed may also be included.

The step of comparing the user's RDA nutritional values and at least one of the user's daily and averaged daily accumulated nutritional values over an interval of time, expressed in units of weight may also be included.

The step of determining the user's daily accumulated net caloric value information for comparison with the user's RDA caloric value information by subtracting the registered daily accumulated caloric value expenditure information regarding selected physical activities from the registered daily accumulated caloric value expenditure information regarding selected foodstuffs and nutrients may also be included. Also included may be the step of estimating at least one of the necessary daily reduction of caloric value information regarding the ingestion of selected foodstuffs and nutrients, to lose a predetermined number of pounds of body weight over a predetermined interval of time; the necessary daily expenditure of caloric value information regarding the selection of physical activities to lose a predetermined number of pounds of body weight over a predetermined interval of time, and a combination of daily reduction of caloric value information regarding the ingestion of selected foodstuffs and nutrients, and daily expenditure of caloric value information regarding the selection of physical activities, to lose a predetermined number of pounds of body weight over a predetermined interval of time by providing means for registering the daily caloric value expenditure necessary to reduce one pound of body weight factored by the predetermined number of pounds of body weight the user desires to lose divided by the user's predetermined interval of time in days displaying related conclusive information.

The step of accessing the at least one database of nutrients, minerals and vitamins to permit accumulation of the value information regarding at least one of selected nutrients, minerals and vitamins to the accumulated nutritional value information of foodstuffs selected may also be included.

The step of exchanging a displayed foodstuff for another foodstuff within the same food group using at least one of the gram weight value information of fat and the total caloric value information of the selected and displayed foodstuff as criteria may also be included.

The step of manually adding to the foodstuff database a foodstuff not included in the foodstuff database along with its corresponding nutritional value information may also be included.

The steps of manually adding to a meal database a meal composed of several foodstuffs, along with corresponding nutritional value information in the meal database and permitting access to the meal as if it were a singular foodstuff may also be included.

The steps of manually adding to a recipe database a recipe composed of several foodstuffs, along with corresponding nutritional value information and permitting access to the recipe as if it were a singular foodstuff may also be included.

The step of providing a warning signal by at least one of: a visual display message and an audible tone regarding selection of a foodstuff whose fat gram weight value information, when added to prior accumulated foodstuff fat gram weight value information, would exceed the user's RDA fat gram weight value information may also be included.

Entry of the user's body weight may be included to correct and update the user's RDA.

A plurality of users may register information simultaneously.

BRIEF DESCRIPTION OF THE DRAWINGS

Some of the objects of the invention having been stated, other objects will appear as the description proceeds, when taken in connection with the accompanying drawings, in which:

FIGS. 2–36 are a series of essentially similar views, all elevation views of a portion of the apparatus of FIG. 1, showing the display screen with a series of messages displayed which illustrated the operation of the apparatus of this invention.

DETAILED DESCRIPTION OF THE PREFERRED EMBODIMENT

Figure 1:
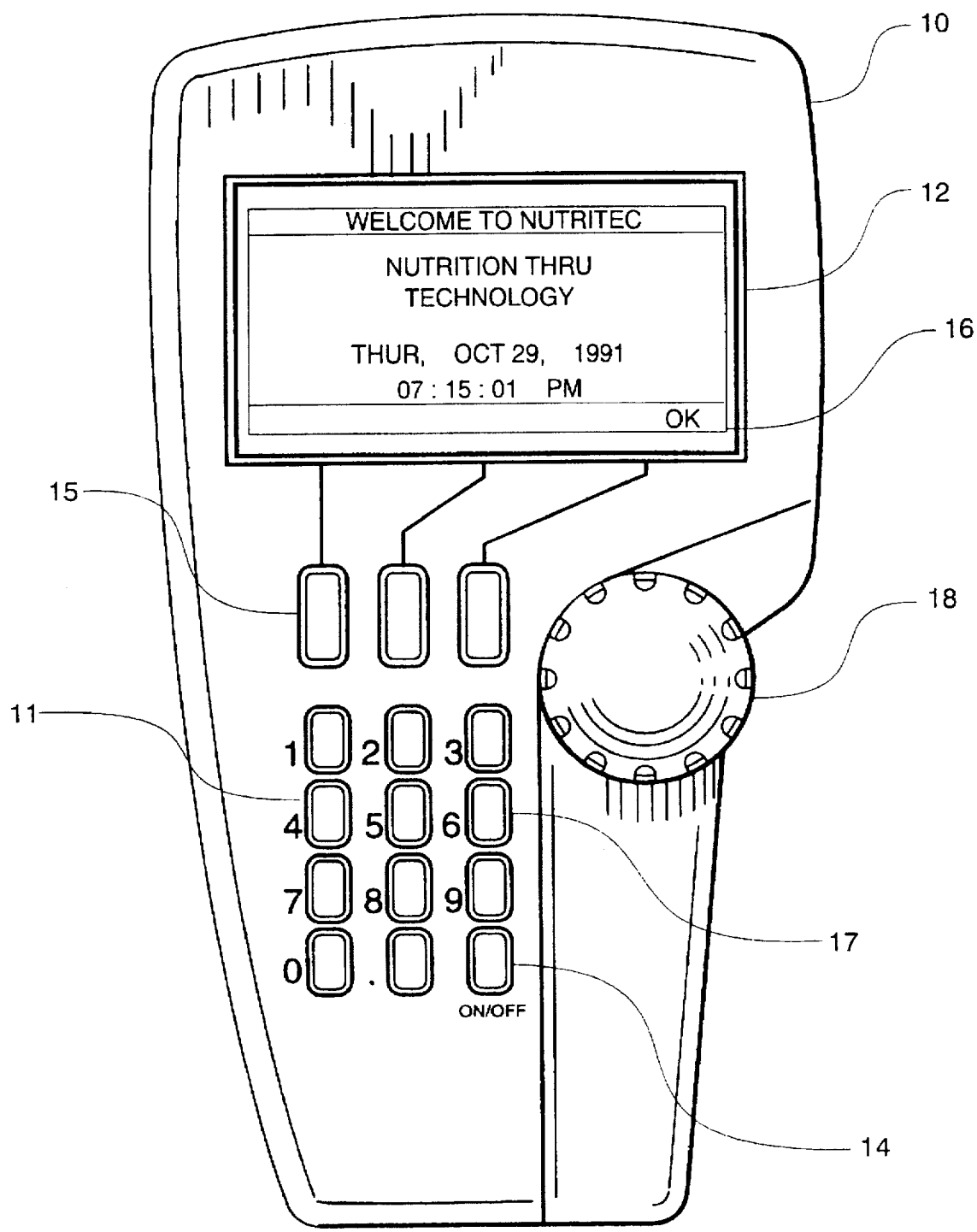
FIG. 1 is an elevation view of one embodiment of the apparatus of this invention, showing the display screen with an introductory message displayed.

While the present invention will be described more fully hereinafter with reference to the accompanying drawings, in which a preferred embodiment of the present invention is shown, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting on the present invention.

Referring now more particularly to the accompanying drawings, one embodiment of the apparatus of the present invention is there shown and generally identified at 10. The series of views included in the drawings, and the description of those views which follows, relate primarily to the messages displayed as the use of the apparatus proceeds. The specific microcomputer chips or elements used to accomplish the purposes which will become more clear as the description proceeds, and the manner of interconnecting those elements, are not shown in detail in the drawings, and specific suggestions for such elements will not be given in the description. One reason for this is that the technology available for hand held microcomputers changes very swiftly, and that which might be used at the time of development of a commercial embodiment of this invention will differ (sometimes markedly) from that available only months later. Another reason is that any person of average skill in the design and application of computer circuitry and software will be able, after understanding the disclosure of the functions, purposes and methods which follows, to select available and suitable elements and construct an operating embodiment of the present invention. By way of only one example, memory chips capable of retaining the digitally stored information which defines the database of nutritional information are available in a range of types, capacities and response times. A capable computer design engineer will be able to select those which represent the most reasonable choice at any given time after studying the disclosure which follows. The same conclusion applies with regard to such elements as the display, keyboard, and so forth.

One embodiment of this invention is a nutritional microcomputer apparatus 10 which has suitable memory means in the form of microchips or microcircuits for receiving and retaining a database of information regarding foodstuffs, a database of information regarding nutrients, a database of information regarding minerals; a database of information regarding vitamins; and a database of information regarding physical activities. An accessing means is provided for accessing from the memory foodstuff identifying information regarding a selected class of foodstuffs from among those in the database, nutrient identifying information regarding a selected nutrient from among those in the database, mineral identifying information regarding a selected mineral from among those in the database, vitamin identifying information regarding a selected vitamin from among those in the database, and physical activity identifying information regarding a selected physical activity from among those in the database. The accessing means preferably takes the form of certain keys on a suitable keyboard 11, which can be of a conductive elastomeric material, a thin film, or some other known keyboard as used on hand held calculators and the like. A display, preferably a liquid crystal display or LCD indicated at 12, is provided for displaying a plurality of lines of information for a corresponding plurality of foodstuffs, nutrients, minerals, vitamins and physical activities accessed from the memory by the accessing keys as described more fully hereinafter. When a display is presented, still other keys of the keyboard 11 function as a selection means for selecting from the display of a plurality of lines of information that foodstuff identifying and nutritional value information which relates to a specific foodstuff, that nutrient identifying and value information which relates to a specific nutrient, that mineral identifying and value information which relates to a specific mineral, that vitamin identifying and value information which relates to a specific vitamin, and that physical activity identifying and value information which relates to a specific activity, as described hereinafter. Finally, the apparatus 10 includes a register means for registering the information selected from the display regarding a specific foodstuff nutrient, mineral, vitamin and physical activity, and for accumulating over an interval of time the information regarding additional selected foodstuffs, nutrients, minerals, vitamins and physical activities. The register means may take the form of memory chips to which power (and thus memory) is continued even while other elements of the microcomputer are unpowered.

It is desirable, in accordance with this invention, that the database of information stored in the memory include information on the caloric, protein, carbohydrate, fat, sodium, cholesterol, fiber, vitamin and mineral content of foodstuffs as well as individual nutrients, minerals, vitamins and physical activities. The nutritional information is entered into and retained in the database in correlation to specific foodstuffs and even to specific brand names of food products, such as Kellogg's brand corn flakes and other cereals, and in correlation to specific serving sizes, such as one cup of cereal.

To activate the apparatus, a user may press the on-off key 14 in the lower right corner of the device illustrated, causing the Welcome Screen shown in FIG. 1 to be displayed.

It is desirable, in accordance with this invention, that information be customized and registered for a plurality of users, each having a particular area of memory as a repository of selected information privy to that individual user. The apparatus should allow the information for each individual user to be separately accessed.

Prior to accessing the information from the databases, a user must initially enter personal and physical identifying information which is registered and used to customize certain subsequent selected information which is distinct and singular to each individual user. With this in mind, provision has been made for the entry of the user's name as the identifier for that user. A user may continue, leaving the Welcome Screen shown in FIG. 1, by pressing a command key 15 on the keyboard 11 located just below the display 12 of the device 10 which will always correspond to the displayed command options menu 16 located on the bottom row of the display 12 of the device 10, causing the User List Screen shown in FIG. 2, permitting a plurality of users, to be displayed. (Upon initialization of name and other personal and physical information by individual users, their names will be displayed on the user list and the user may then just select his name for continuation; however, the initial usage of this invention requires entry of identifying information, both personal and physical.) A user will initially select a line on the user list as not used, by a command key 15, causing the Physical Information Screen shown in FIG. 3 to be displayed. The user's name, age, sex, height, weight, and lifestyle activity level (very light, light, moderate, heavy) is entered by command keys 15 and numerical keys 17 (on the keyboard 11, located in the middle of the device 10) shown by example in FIG. 4. The entered personal and physical information is reviewed on the display 12 by the user and corrections, if any, are made. Completed acceptable information is registered by pressing the appropriate command key 15. Using the Harris-Benedict equation and the user's registered personal and physical data information, the user's RDA (recommended daily allowance) is computed with appropriate components and programs contained within apparatus 10, and illustrated in FIG. 5, showing the recommended daily maintenance values of the user regarding caloric and nutritional information. The establishment of the user's RDA provides a means of comparison regarding user daily nutritional consumption and physical activities. Pressing the appropriate command key 15 will display the Primary Menu Screen in the present illustrated embodiment of FIG. 6.

In accessing information from the databases, a user will first select from among the information retained in memory those elements of information which relate to a selected operation of the apparatus initiated from the Primary Menu Screen and then from among the information retained in memory those elements of information which relate to a selected operation of the apparatus initiated from other sequential and related menu screen, refining the intended section process.

It is desirable, in accordance with this invention, to afford the user ease of access to the large amount of information registered in the databases regarding foodstuffs, nutrients, minerals, vitamins and physical activities by apparatus means of a scrolling knob 18 located on the keyboard 11 of the device 10 illustrated, permitting rapid retrieval of the desired information.

Figure 6:
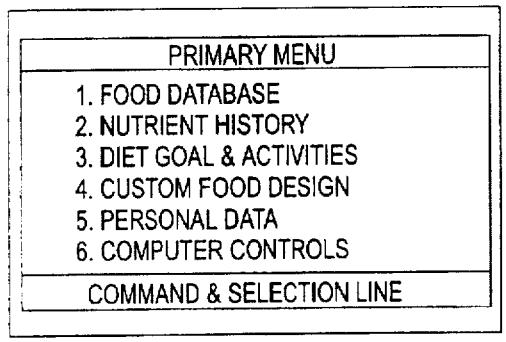
Figure 7:
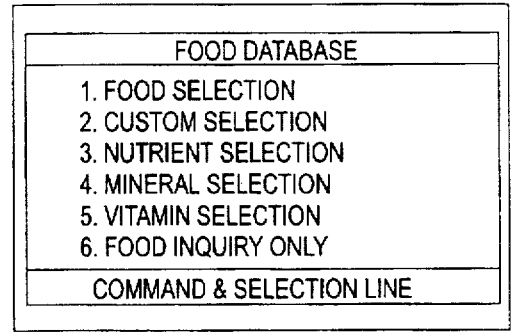
Figure 8:
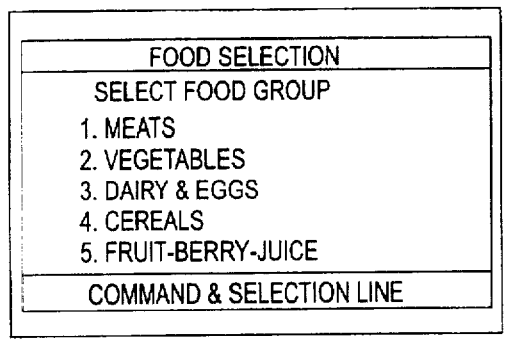
Figure 9:
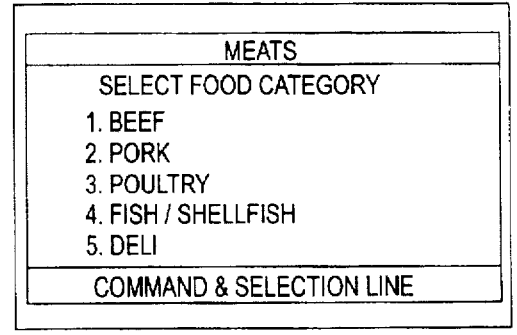
Figure 14:
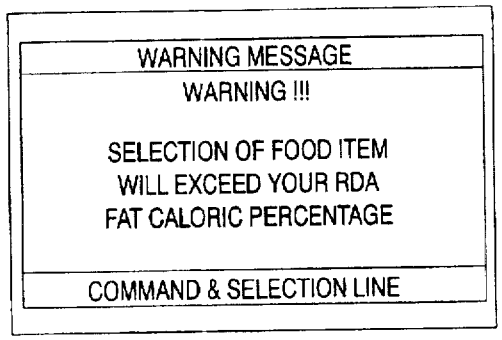
Figure 15:
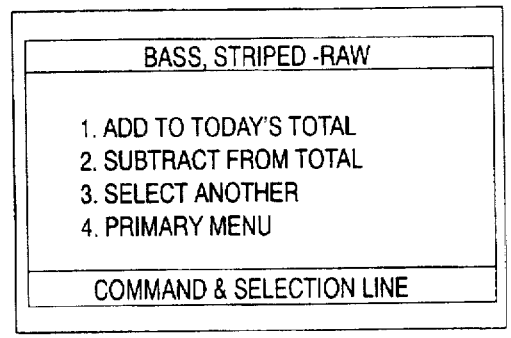
Figure 16:
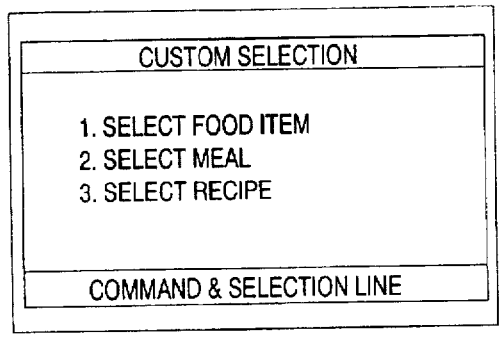

Beginning at the Primary Menu Screen, displaying options such as those shown in the present illustrated embodiment of FIG. 6, a user may desire to select, view and register into memory daily ingestion of foodstuffs along with associated identifying information regarding nutrients, minerals and vitamins, by choosing Food Database by pressing the scrolling knob 18, moving the highlighted cursor to that selection, and pressing the appropriate command key 15 displaying options such as those shown in the present illustrated embodiment of FIG. 7. A user may then wish to choose Food Selection by pressing the scrolling knob 18, moving the highlighted cursor to that selection, and pressing the appropriate command key 15 displaying Food Group selection options such as those shown in the present illustrated embodiment of FIG. 8. A user may then wish to choose Meats by pressing the scrolling knob 18, moving the highlighted cursor to that selection, and pressing the appropriate command key 15 displaying Food Category selection options such as those shown in the present illustrated embodiment of FIG. 9. A user may then wish to choose Fish/Shellfish by pressing the scrolling knob 18, moving the highlighted cursor to the foodstuff item selection of Bass, Striped-Raw, where it is entirely possible, in accordance with this invention, for the user to press the command key 15 SWAP, displaying a listing of foodstuff items within the same Food Group, in descending order, those foodstuff items which most closely approximate the highlighted selection, first as to the identifying nutrient value of Fat and second as to the identifying total caloric value, as shown in the present illustrated embodiment of FIG. 11. Having selected the foodstuff item by pushing the appropriate command key 15, it is entirely possible, in accordance with this invention, for the user to modify the portion or size of the selected foodstuff, by pressing the appropriate numeric keys 17, as shown in the present illustrated embodiment of FIG. 12. By pushing the appropriate command key 15, the selected and modified foodstuff item is displayed featuring the foodstuff name, source of identifying value information, the modified size of the portion, percentages of fat calories, carbohydrate calories and protein calories as compared to total calories and identifying value information regarding associated nutrients, minerals and vitamins, as shown in the present illustrated embodiment of FIG. 13. At this point, if the caloric value information of the selected foodstuff, when accumulated with previously selected and registered foodstuffs of the same day, should exceed the RDA of the user, an audible and/or displayed warning would inform the user, such as that which is shown in the present embodiment of FIG. 14. By pressing the appropriate command key 15, options, as shown in the present illustrated embodiment of FIG. 15, are afforded a user by pressing the scrolling knob 18, moving the highlighted cursor to a selected option, and pressing the appropriate command key 15, to either: add the foodstuff selection to today's accumulated and registered total; subtract the foodstuff selection from today's accumulated and registered total; select another foodstuff item by returning to the Food Database display FIG. 7; or returning to the Primary Menu FIG. 6.

Returning to, by pressing the appropriate command key 15, and starting from the Food Database display FIG. 7, a user may desire to select, view and register into memory daily ingestion of custom foodstuffs designed by the user, along with associated identifying information regarding nutrients, minerals and vitamins, by choosing Custom Selection by pressing the scrolling knob 18, moving the highlighted cursor to that selection, and pressing the appropriate command key 15 displaying options such as those shown in the present illustrated embodiment of FIG. 7. A user may then wish to select Food Item, Meal or Recipe, all three of which are composed of foodstuffs selected from the foodstuffs database as described hereinafter.

Figure 17:
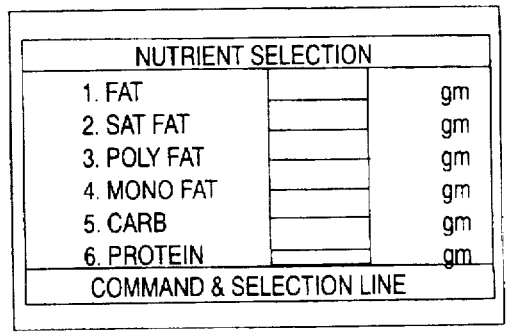

Returning to, by pressing the appropriate command key 15, and starting from the Food Database display FIG. 7, a user may desire to select, view and register into memory daily ingestion of individual nutrient values, along with associated identifying information regarding nutrients selected from among those in the mineral database, such as those shown in the present illustrated embodiment of FIG. 17, by pressing the scrolling knob 18, moving the highlighted cursor to the selection, entering value information with numeric keys 17 and pressing the appropriate command key 15.

Returning to, by pressing the appropriate command key 15, and starting from the Food Database display FIG. 7, a user may desire to select, view and register into memory daily ingestion of individual mineral values, along with associated identifying information regarding minerals selected from among those in the mineral database, such as those shown in the present illustrated embodiment of FIG. 18, by pressing the scrolling keys 18, moving the highlighted cursor to the selection, entering value information with numeric keys 17 and pressing the appropriate command key 15.

Returning to, by pressing the appropriate command key 15, and starting from the Food Database display FIG. 7, a user may desire to select, view and register into memory daily ingestion of individual vitamin values, along with associated identifying information regarding vitamins selected from among those in the vitamin database, such as those shown in the present illustrated embodiment of FIG. 19, by pressing the scrolling knob 18, moving the highlighted cursor to the selection, entering value information with the numeric keys 17 and pressing the appropriate command key 15.

Returning to, by pressing the appropriate command key 15, and starting from the Food Database display FIG. 7, a user may desire to select and view foodstuffs along with associated identifying information regarding nutrients, minerals and vitamins, without registering this information into memory but only to satisfy an inquiry concerning that foodstuff, by pressing the scrolling knob 18, moving the highlighted cursor to the selection Food Inquiry Only as shown in the present illustrated embodiment of FIG. 20, and pressing the appropriate command key 15. Further apparatus methods of operation and procedures required are identical to those used in Food Selection describe above, and as shown in the present illustrated embodiments of FIGS. 8–13.

Beginning again at the Primary Menu Screen, by pressing the appropriate command key 15, displaying options such as those shown in the present illustrated embodiment of FIG. 6, a user may desire to view the averaged registered accumulated daily ingestion of selected foodstuffs along with associated identifying information regarding nutrients, minerals and vitamins, over an interval of time, by choosing Nutrient History by pressing the scrolling knob 18, moving the highlighted cursor to that selection, and pressing the appropriate command key 15 displaying options such as those shown in the present illustrated embodiment of FIG. 21. A user may then wish to choose Average Consumption by pressing the scrolling knob 18, moving the highlighted cursor to that selection, and pressing the appropriate command key 15, initiating a display by which a user could choose that day's, or an average of days over an interval of time, by pressing the appropriate numeric keys 17 and command keys 15, accumulated nutritional value information regarding previously selected foodstuffs, nutrients, minerals, vitamins and physical activities, as shown in the present illustrated embodiment of FIG. 22.

Returning to, by pressing the appropriate command key 15, and starting from the Nutrient History display FIG. 21, a user may then wish to choose RDA Comparison by pressing the scrolling knob 18, moving the highlighted cursor to that selection, and pressing the appropriate command key 15, initiating a display by which a user could choose that day's, or an average of days over an interval of time, by pressing the appropriate numeric keys 17 and command keys 15, accumulated nutritional value information regarding previously selected foodstuffs, nutrients, minerals, vitamins, and physical activities, making comparison to the user's RDA as shown in the present illustrated embodiment of FIG. 23.

Beginning again at the Primary Menu Screen, by pressing the appropriate command key 15, displaying options such as those shown in the present illustrated embodiment of FIG. 6, a user may desire to design a personal diet or weight loss regiment by selecting Diet Goal & Activities, by pressing the scrolling knob 18, moving the highlighted cursor to a selected option, and pressing the appropriate command key 15, displaying options as shown in the present illustrated embodiment of FIG. 24. A user may wish to choose Diet Goals by pressing the scrolling knob 18, moving the highlighted cursor to that selection, and pressing the appropriate command key 15, whereby a display is initiated by which a user could then select, the desired pounds of body weight loss and the desired interval of time for that loss, by pressing the appropriate numeric keys 17 and command keys 15, and, in accordance with this invention, the number of calories necessary to delete from the user's daily diet to achieve the desired goal would be displayed as shown in the present illustrated embodiment of FIG. 25. By pressing the appropriate command key 15, a displayed message would appear reporting to the user dietary and physical activity options, as shown in the present illustrated embodiment of FIG. 26.

Returning to, by pressing the appropriate command key 15, and starting from the Diet Goal & Activities display FIG. 24, a user may then wish to choose Activities List by pressing the scrolling knob 18, moving the highlighted cursor to that selection, and pressing the appropriate command key 15, initiating a display, as shown in the present illustrated embodiment of FIG. 27, listing physical activities by which a user could select a physical activity, by pressing the scrolling knob 18, moving the highlighted cursor to that selection, and pressing the appropriate command key 15, and entering the number of minutes exercised or to be exercised, by pressing the appropriate numeric keys 17, and command keys 15, registering the physical activity caloric value expenditure information. By pressing the appropriate command key 15, a display is initiated: showing today's accumulated nutritional value information regarding previously selected foodstuffs, nutrients, minerals, and vitamins; showing today's accumulated caloric value expenditure information regarding previously selected physical activities; and showing today's net caloric totals which is computed, in accordance with this invention, by subtracting today's net caloric totals which is computed, in accordance with this invention, by subtracting today's accumulated caloric value expenditure information regarding previously selected physical activities, from today's accumulated nutritional value information regarding previously selected foodstuffs, nutrients, minerals, and vitamins, as shown in the present illustrated embodiment of FIG. 28. The updated "net caloric total" is also shown in the present illustrated embodiment of Average Consumption FIG. 22, and RDA Comparison, FIG. 23. By pressing the appropriate command key 15, options, as shown in the present illustrated embodiment of FIG. 29, are afforded a user by pressing the scrolling knob 18, moving the highlighted cursor to a selected option, and pressing the appropriate command key 15, to either: add the physical activity selection to today's accumulated and registered total; subtract the physical activity selection from today's accumulated and registered total; select another physical activity by returning the Activities List display FIG. 27; or returning to the Primary Menu FIG. 6.

Beginning again at the Primary Menu Screen, by pressing the appropriate command key 15, displaying options such as those shown in the present illustrated embodiment of FIG. 6, a user may desire to incorporate foodstuff items and perhaps even entire meals and recipes, along with associated identifying value information regarding nutrients, minerals, and vitamins, that are not registered in the computer database, by choosing Custom Food Design, by pressing the scrolling knob 18, moving the highlighted cursor to a selected option, and pressing the appropriate command key 15, displaying options such as those shown in the present illustrated embodiment of FIG. 30. A user may then wish to choose Add Food, by pressing the scrolling knob 18, moving the highlighted cursor to the selected option, pressing the appropriate command key 15, displaying options such as those shown in the present illustrated embodiment of FIG. 31, initiating a display requiring user entry of food name and identifying value information regarding nutrients, minerals and vitamins, which is then registered into a database for user entered foodstuffs by pressing the appropriate command key 15.

Returning to, by pressing the appropriate command key 15, and starting from the Custom Food Design display FIG. 30, a user may then wish to choose Add Meal by pressing the scrolling knob 18, moving the highlighted cursor to that selection, and pressing the appropriate command key 15, initiating a display, as shown in the present illustrated embodiment of FIG. 32, initiating a display requiring user entry of meal name and identifying value information of selected foodstuffs resident in the foodstuff database regarding nutrients, minerals and vitamins, which is then registered into a database for user entered meals by pressing the appropriate command key 15.

Returning to, by pressing the appropriate command key 15, and starting from the Custom Food Design display FIG. 30, a user may then wish to choose Add Recipe by pressing the scrolling knob 18, moving the highlighted cursor to that selection, and pressing the appropriate command key 15, initiating a display, as shown in the present illustrated embodiment of FIG. 33, initiating a display requiring user entry of recipe name and identifying value information of selected foodstuffs resident in the foodstuff database regarding nutrients, minerals and vitamins, which is then registered into a database for user entered recipes by pressing the appropriate command key.

Beginning again at the Primary Menu Screen, by pressing the appropriate command key 15, displaying options such as those shown in the present illustrated embodiment of FIG. 6, a user may desire to view the accumulated history over an interval of time of previously selected and registered nutritional information as well as registering and viewing the accumulated history over an interval of time of personal body weight by choosing Personal Data, by pressing the scrolling knob 18, moving the highlighted cursor to a selected option, and pressing the appropriate command key 15, displaying options such as those shown in the present illustrated embodiment of FIG. 34. A user may then wish to choose Physical Information by pressing the scrolling knob 18, moving the highlighted cursor to the selected option, and pressing the appropriate command key 15, initiating a display such as that shown in the present illustrated embodiment of FIG. 4.

Returning to, by pressing the appropriate command key 15, and starting from the Personal Data display FIG. 34, a user may then wish to choose Personal RDA, by pressing the scrolling knob 18, moving the highlighted cursor to the selected option, and pressing the appropriate command key 15, initiating a display such as that shown in the present illustrated embodiment of FIG. 5.

Returning to, by pressing the appropriate command key 15, and starting from the Personal Data display FIG. 34, a user may then wish to choose Weight Record, by pressing the scrolling knob 18, moving the highlighted cursor to the selected option, and pressing the appropriate command key 15, initiating a display affording user options of entering present body weight, which is registered into memory, or view an average body weight history of the user over an interval of time, by pressing the appropriate numeric keys 17, and command keys 15, such as that shown in the present illustrated embodiment of FIG. 35.

Beginning again at the Primary Menu Screen, by pressing the appropriate command key 15, displaying options such as those shown in the present illustrated embodiment of FIG. 6, a user may desire to view and/or reset the computer settings regarding time, date, contrast, and auto off, by choosing Computer Controls by pressing the scrolling knob 18, moving the highlighted cursor to a selected option, and pressing the appropriate command key 15, displaying options such as those shown in the present illustrated embodiment of FIG. 36. A user may then wish to choose Time, by pressing the scrolling knob 18, moving the highlighted cursor to the selected option, pressing the appropriate numeric keys 17, and command keys 15, resetting the computer to the desired time, which is then registered into memory by pressing the appropriate command key 15.

Returning to, by pressing the appropriate command key 15, and starting from the Computer Controls display FIG. 36, a user may then wish to choose Date, by pressing the scrolling knob 18, moving the highlighted cursor to the selected option, pressing the appropriate numeric keys 17, and command keys 15, resetting the computer to the desired date, which is then registered into memory by pressing the appropriate command key 15.

Returning to, by pressing the appropriate command key 15, and starting from the Computer Controls display FIG. 36, a user may then wish to choose Contrast, by pressing the scrolling knob 18, moving the highlighted cursor to the selected option, pressing the appropriate numeric keys 17, and command keys 15, resetting the computer display to the desired contrast level, which is then registered into memory by pressing the appropriate command key 15.

Returning to, by pressing the appropriate command key 15, and starting from the Computer Controls display FIG. 36, a user may then wish to choose Auto Off, by pressing the scrolling knob 18, moving the highlighted cursor to the selected option, pressing the appropriate numeric keys 17, and command keys 15, resetting the desired number of seconds of computer inactivity required before automatic termination of the session, which is then registered into memory by pressing the appropriate command key 15.

In the drawings and specifications there has been set forth a preferred embodiment of the invention and, although specific terms are used, the description thus given uses terminology in a generic and descriptive sense only, and not for purposes of limitation.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A hand held nutritional microcomputer apparatus comprising:

memory means for receiving and retaining a database of information for a plurality of foodstuffs, a database of information for a plurality of nutrients, a database of information for a plurality of minerals, a database of information for a plurality of vitamins, and a database of information for a plurality of physical activities;

display means for selectively displaying a food item selection screen including a plurality of foodstuffs, a nutrient selection screen including a plurality of nutrients, a mineral selection screen including a plurality of minerals, a vitamin selection screen including a plurality of vitamins, and an activities selection screen including a plurality of physical activities;

selection means for selecting from said display means a displayed foodstuff from said displayed food item selection screen, a displayed nutrient from said displayed nutrient selection screen, a displayed mineral from said displayed mineral selection screen, a vitamin from said displayed vitamin selection screen, and a displayed physical activity from said displayed activity screen;

accessing means for accessing from said memory means
      (i) nutritional value information per unit serving regarding a selected foodstuff, and
      (ii) physical activity value information per unit time regarding a selected physical activity;

entering means for entering
      (i) the serving size of a selected foodstuff for modifying the accessed value information for that selected foodstuff, said modification comprising factoring said accessed value information by said serving size,
      (ii) the time of a selected physical activity for modifying the accessed value information for that selected physical activity, said modification comprising factoring said accessed value information by said time,
      (iii) nutrient value information for a selected nutrient, the nutrient value information comprising unit ingestion of that nutrient,
      (iv) mineral value information for a selected mineral, the mineral value information comprising unit ingestion of that mineral, and
      (v) vitamin value information for a selected vitamin, the vitamin value information comprising unit ingestion of that vitamin; and register means for registering in said memory means said modified value information of said selected foodstuff, said modified value information of said selected physical activity; said entered value information for said selected nutrient, said entered value information for said selected mineral, and said entered value information for said selected vitamin, and for accumulating in said memory means over an interval of time additional registered value information.

2. Apparatus according to claim 1 wherein said accessing means selects from among the foodstuffs retained in said foodstuff database those foodstuffs whose nutritional value information have related elements of information thereby grouping related foodstuffs together, and said display means displays each group of related foodstuffs.

3. Apparatus according to claim 2 wherein said display means displays a predetermined number of lines of information each having a predetermined number of characters and further wherein said accessing means causes the display of a plurality of foodstuffs absent nutritional value information, and a plurality of physical activities absent physical activity value information.

4. Apparatus according to claim 1 wherein said register means accumulates totals of value information registered for all of said selected foodstuffs, each of said nutrients, each of said minerals, each of said vitamins, and all of said selected physical activities over at least one of daily intervals and an accumulation of daily intervals.

5. Apparatus according to claim 1 wherein said database of information for said plurality of said foodstuffs includes caloric, protein, carbohydrate, fat, sodium, cholesterol, and fiber content per unit serving information for each said foodstuff.

6. Apparatus according to claim 1 wherein said database of information for said plurality of said foodstuffs includes mineral content per unit serving information for at least one mineral for each said foodstuff.

7. Apparatus according to claim 1 wherein said database of information for said plurality of said foodstuffs includes vitamin content per unit serving information for at least one vitamin for each said foodstuff.

8. Apparatus according to claim 1 wherein said database of information for said plurality of said foodstuffs includes the brand names of at least some of said foodstuffs.

9. Apparatus according to claim 1 wherein said register means accumulates totals of at least one of the group of protein content, carbohydrate content, fat content, sodium content, cholesterol content, fiber content, mineral content, and vitamin content ingested over at least one of the group of daily intervals and an accumulation of daily intervals.

10. Apparatus according to claim 1 wherein said register means accumulates totals of modified value information comprising caloric content of all selected foodstuffs and modified value information comprising caloric expenditures of all selected physical activities over at least one of the group of daily intervals and an accumulation of daily intervals.

11. A method of recording information for foodstuffs, nutrients, minerals, and vitamins selected for consumption and the caloric expenditure of physical activity, comprising the steps of:

entering into and retaining in memory a database of nutritional value information for a plurality of foodstuffs, a database of nutrient value information for a plurality of nutrients, a database of mineral value information for a plurality of minerals, a database of vitamin value information for a plurality of vitamins, and a database of physical activity value information for a plurality of physical activities;

selectively displaying a food item selection screen including foodstuffs, a nutrient selection screen including nutrients, a mineral selection screen including minerals, a vitamin selection screen including vitamins, and an activities selection screen including physical activities;

selecting from the display one of the group of a displayed foodstuff from said displayed food item selection screen, a displayed nutrient from said displayed nutrient selection screen, a displayed mineral from said displayed mineral selection screen, a displayed vitamin from said displayed vitamin selection screen, and a displayed physical activity from said displayed activity screen;

accessing from memory nutritional value information for a foodstuff upon selection of that foodstuff, and physical activity value information for a physical activity upon selection of that physical activity;

entering one of the group of
    the serving size of a foodstuff upon selection of that foodstuff for modifying the accessed nutritional value information for that selected foodstuff,
    the time of a physical activity upon selection of that physical activity for modifying the accessed physical activity value information for that selected physical activity,
    nutrient value information for a selected nutrient upon selection of that nutrient,
    mineral value information for a selected mineral upon selection of that mineral, and
    vitamin value information for a selected vitamin upon selection of that vitamin; and registering in the memory means one of the group of modified value information of a selected foodstuff, entered value information of a selected nutrient, entered value information of a selected mineral, entered value information of a selected vitamin, and modified value information of a selected physical activity, and accumulating over an interval of time additional registered value information.

12. A method according to claim 11 wherein said step of entering into and retaining in memory a database of nutritional value information for said plurality of foodstuffs includes entering and retaining information regarding the caloric content per unit serving of each said foodstuff.

13. A method according to claim 11 wherein said step of entering into and retaining in memory a database of nutritional value information for said plurality of foodstuffs includes entering and retaining information regarding the protein content per unit serving of each said foodstuff.

14. A method according to claim 11 wherein said step of entering into and retaining in memory a database of nutritional value information for said plurality of foodstuffs includes entering and retaining information regarding the carbohydrate content per unit serving of each said foodstuff.

15. A method according to claim 11 wherein said step of entering into and retaining in memory a database of nutritional value information for said plurality of foodstuffs includes entering and retaining information regarding the fat content per unit serving of each said foodstuff.

16. A method according to claim 11 wherein said step of entering into and retaining in memory a database of nutritional value information for said plurality of foodstuffs includes entering and retaining information regarding the sodium content unit serving of each said foodstuff.

17. A method according to claim 11 wherein said step of entering into and retaining in memory a database of nutritional value information for said plurality of foodstuffs includes entering and retaining information regarding the cholesterol content per unit serving of each said foodstuff.

18. A method according to claim 11 wherein said step of entering into and retaining in memory a database of nutritional value information for said plurality of foodstuffs includes entering and retaining information regarding the fiber content unit serving of each said foodstuff.

19. A method according to claim 11 wherein said step of entering into and retaining in memory a database of nutritional value information for said plurality of foodstuffs includes entering and retaining information regarding the mineral content per unit serving of each said foodstuff.

20. A method according to claim 11 wherein said step of entering into and retaining in memory a database of nutritional value information for said plurality of foodstuffs includes entering and retaining information regarding the vitamin content per unit serving of each said foodstuff.

21. A method according to claim 11 wherein said step of entering into and retaining in memory a database of physical activity value information for said plurality of physical activities includes entering and retaining information regarding the caloric expenditure values per unit time for each physical activity.

22. A method according to claim 11 wherein said step of entering into and retaining in memory a database of nutritional value information for said plurality of foodstuffs includes entering and retaining information regarding the brand names of foodstuffs.

23. A method according to claim 11 wherein said step of accessing nutritional value information comprises selecting from among the foodstuffs retained in said foodstuff database those foodstuffs whose nutritional value information have related elements of information thereby grouping related foodstuffs together, and said step of displaying includes selectively displaying each group of related foodstuffs.

24. A method according to claim 23 wherein said step of accessing nutritional value information comprises selecting from among the foodstuffs retained in said foodstuff database those food groups whose nutritional value information have related elements of information thereby grouping related food groups together in a series, and said step of displaying includes displaying each series of related food groups.

25. A method according to claim 11 wherein said step of accessing information causes the display of one of the group of nutritional value information for a single selected foodstuff and physical activity value information for a single selected physical activity.

26. A method according to claim 11 wherein said step of registering comprises accumulating totals of nutritional value information of all selected foodstuffs, accumulating total nutrient value information for each selected nutrient, accumulating total mineral value information for each selected mineral, accumulating total vitamin value information for each selected vitamin, and accumulating total physical activity value information for all selected physical activities over at least one of: daily intervals and an accumulation of daily intervals.

27. A method according to claim 26 further comprising the step of accumulating the registered value information regarding at least one of the group of selected nutrients, selected minerals and selected vitamins with the accumulated nutritional value information of all selected foodstuffs.

28. A method according to claim 11 further comprising the step of: computing the user's RDA of value information regarding nutrients, minerals, vitamins and physical activities using the Harris-Benedict Equation, by entering the user's personal and physical characteristics regarding age, sex, weight, height and activity level, and registering said RDA value information in a user database from which it may be accessed and displayed.

29. A method according to claim 28 further comprising the step of: comparing the user's RDA nutritional values and at least one of the user's daily and averaged daily accumulated nutritional values over an interval of time, expressed in units of weight.

30. A method according to claim 28 further comprising the step of: providing a warning signal by at least one of: a visual display message and an audible tone regarding selection of a foodstuff whose fat gram weight value information, when added to prior accumulated foodstuff fat gram weight value information, would exceed the user's RDA fat gram weight value information.

31. A method according to claim 28 including entering a user's updated body weight to correct and update the user's RDA.

32. A method according to claim 28 including the step of registering characteristics for a plurality of users.

33. A method according to claim 11 further comprising the step of: computing the user's accumulated registered value information of calories, fat, carbohydrates and protein each as a percentage of total calories of the caloric sum as well as gram weight value information, and registering and displaying said information as daily value information and/or averaged daily value information over an interval of time.

34. A method according to claim 11 further comprising the steps of: computing the use's caloric expenditure value, regarding a selected physical activity from among those in the physical activity database, by factoring the weight of the user, the number of minutes exercised and the pre-established hourly rate of caloric expenditure for each physical activity, and registering said caloric expenditure in a user database from which it may be accessed and displayed.

35. A method according to claim 11 further comprising the step of: determining the user's daily accumulated net caloric value information for comparison with the user's RDA caloric value information by subtracting the registered daily accumulated caloric value expenditure information regarding selected physical activities from the registered daily accumulated caloric value information regarding selected foodstuffs and nutrients.

36. A method according to claim 11 further comprising the steps of: estimating at least one of the necessary daily reduction of caloric value information regarding the ingestion of selected foodstuffs and nutrients to lose a predetermined number of pounds of body weight over a predetermined interval of time; the necessary daily expenditure of caloric value information regarding the selection of physical activities to lose a predetermined number of pounds of body weight over a predetermined interval of time and a combination of daily reduction of caloric value information regarding the ingestion of selected foodstuffs and nutrients, and daily expenditure of caloric value information regarding the selection of physical activities, to lose a predetermined number of pounds of body weight over a predetermined interval of time, and displaying the daily caloric value expenditure necessary to reduce one pound of body weight factored by the predetermined number of pounds of body weight the user desires to lose divided by the user's predetermined interval of time.

37. A method according to claim 11 further comprising the step of: exchanging a displayed foodstuff for another foodstuff using as exchange criteria at least one of the group of the gram weight value information of fat per unit serving and the total caloric value information per unit serving of the selected and displayed foodstuff.

38. A method according to claim 11 further comprising the step of: manually adding to the foodstuff database a foodstuff not included in the foodstuff database along with its corresponding nutritional value information.

39. A method according to claim 11 further comprising the steps of: entering into and retaining in memory a database of information regarding nutritional value information for a plurality of meals, each meal comprising several foodstuffs, and manually adding to the meal database a meal not included in the meal database along with its nutritional value information and permitting access to the meal as if it were a singular foodstuff.

40. A method according to claim 11 further comprising the steps of: entering into and retaining in memory a database of information regarding nutritional value information for a plurality of recipes, each recipe comprising several foodstuffs, and manually adding to the recipe database a recipe not included in the recipe database along with its nutritional value information and permitting access to the recipe as if it were a singular foodstuff.

41. A hand held nutritional microcomputer apparatus comprising:

memory means for receiving and retaining a database of information including caloric content per unit serving regarding foodstuffs, and a database of information including caloric expenditure per unit time regarding physical activities;

display means for selectively displaying a plurality of foodstuffs and a plurality of physical activities;

selection means for selecting from said display means a displayed foodstuff and, alternatively; a displayed physical activity;

accessing means for accessing from said memory means nutritional value information per unit serving regarding a selected foodstuff, and for accessing from said memory means physical activity value information per unit time regarding a selected physical activity;

entering means for entering
(i) the unit serving size of a selected foodstuff for modifying the accessed value information for that foodstuff, including the computing of the calories ingested for that foodstuff by multiplying said entered unit serving size by said accessed caloric content per unit serving, and
(ii) the time of a selected physical activity exercised for modifying the accessed value information for that physical activity, including the computing of the calories expended for that physical activity by multiplying said entered time by said accessed caloric expenditure per unit time; and register means for registering in said memory means value information of selected foodstuff and selected physical activity, and for accumulating over an interval of time additional registered value information.

42. A hand held nutritional microcomputer apparatus comprising:

memory means for receiving and retaining a database of value information regarding nutrients, a database of value information regarding minerals, and a database of value information regarding vitamins;

display means for displaying a nutrient selection screen including nutrients, a mineral selection screen including minerals, and a vitamin selection screen including vitamins;

selection means for selecting from said display means one of the group of a displayed nutrient from said nutrient selection screen, a displayed mineral from said mineral selection screen, and a displayed vitamin from said vitamin selection screen;

entering means for entering value information for said selected one of the group of a displayed nutrient from said nutrient selection screen, a displayed mineral from said mineral selection screen, and a displayed vitamin from said vitamin selection screen; and register means for registering in said memory means said value information entered for said selected one of the group of a displayed nutrient from said nutrient selection screen, a displayed mineral from said mineral selection screen, and a displayed vitamin from said vitamin selection screen, and for accumulating over an interval of time additional value information registered therefor.

\* \* \* \* \*

UNITED STATES PATENT AND TRADEMARK OFFICE
CERTIFICATE OF CORRECTION

PATENT NO. : 5,704,350
DATED : January 6, 1998
INVENTOR(S) : William B. Williams It is certified that error appears in the above-identified patent and that said Letters Patent is hereby corrected as shown below:

Column 12, line 31, after "information." insert new copy (See A-1) -- The Harris-Benedict Equation is well known in the art and has been the standard for determining basal energy or caloric requirements for individuals since 1919, and is listed in almost every clinical nutritional manual and textbook, such as, for example, KRAUSE & MAHON, FOOD NUTRITION & DIET THERAPY, p. 15 (7th ed.). There are two forms of the equation, i.e., one for men and one for women:

Women: $[655 + (9.6 \times W) + (1.7 \times H) - (4.7 \times A)] \times$ Factor

Men: $[66 + (13.7 \times W) + (5 \times H) - (6.8 \times A)] \times$ Factor where W is the person's weight (kgm), H is the person's height (cm), and A is the person's Age (years). Factor is the relative activity factor and is 1.2 if the person does not activity, 1.3 if the person does light activity, 1.4 if the person does moderate activity, and 1.5 if the person does heavy activity. --

Column 18, line 29, delete "a vitamin" and insert -- a displayed vitamin --
Column 18, line 59, delete "activity;" and insert -- activity, --
Column 20, line 14, all of line 14 should be on line 13, following "value"
Column 20, line 57, delete "unit" and insert -- per unit --
Column 20, line 67, delete "unit" and insert -- per unit --
Column 22, line 47, delete "time" and insert -- time; --
Column 23, line 28, delete "alternatively;" and insert -- alternatively, --
Column 24, line 8, before "value" insert -- modified --

Signed and Sealed this

Sixteenth Day of March, 1999

Attest:

Q. TODD DICKINSON

Attesting Officer

Acting Commissioner of Patents and Trademarks